United States Patent
Chartrain et al.

[11] Patent Number: 5,792,871
[45] Date of Patent: Aug. 11, 1998

[54] PROCESS FOR N-BOC-N-(R)-2(3-PYRIDYL)-2-HYDROXY-ETHYL)-N-2(4-AMINOPHENYL) ETHYL AMINE AND 2-(4-AMINOPHENYL)-N-2-(2(R)-HYDROXY-2-PHYRIDIN-S-YL-ETHYL)ACETAMIDE

[75] Inventors: Michel M. Chartrain; Christopher Roberge, both of Westfield; John Y. L. Chung, Edison; Dalian Zhao, Fanwood, all of N.J.

[73] Assignee: Merck & Co., Inc., Rahway, N.J.

[21] Appl. No.: 882,977

[22] Filed: Jun. 26, 1997

Related U.S. Application Data

[60] Provisional application No. 60/022,056 Jul. 22, 1996.
[51] Int. Cl.⁶ ............................................. C07D 213/30
[52] U.S. Cl. ........................ 546/335; 546/336; 435/122
[58] Field of Search ............................ 546/335, 336

[56] References Cited

U.S. PATENT DOCUMENTS 5,541,197 7/1996 Fisher .................................. 514/311

*Primary Examiner*—Jane Fan
*Attorney, Agent, or Firm*—Mollie M. Yang; David L. Rose

[57] ABSTRACT

Compound 9 is prepared by a 9-step

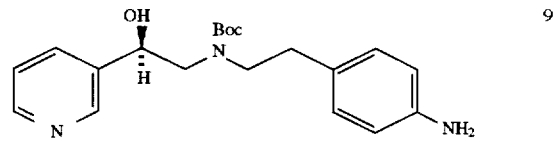

process in an overall yield of about 35% from 3-acetylpyridine.

Compound 10 is prepared by a seven-step

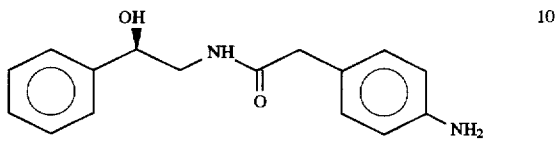

process in an overall yield of about 30% from 3-acetyl pyridine. These compounds are key intermediates in the synthesis of Compound 11, an important β-3 agonist useful in the treatment of obesity and diabetes.

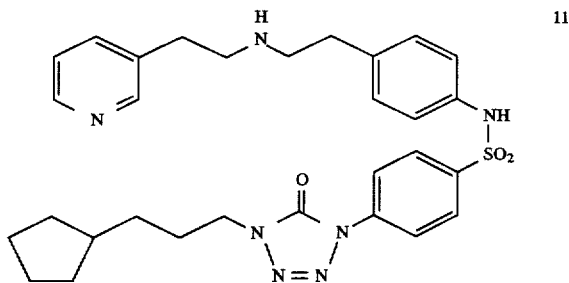

2 Claims, No Drawings

PROCESS FOR N-BOC-N-(R)-2(3-PYRIDYL)-2-HYDROXY-ETHYL)-N-2(4-AMINOPHENYL) ETHYL AMINE AND 2-(4-AMINOPHENYL)-N-2-(2(R)-HYDROXY-2-PHYRIDIN-S-YL-ETHYL)ACETAMIDE

CROSS REFERENCE TO RELATED APPLICATIONS

This application is based on, and claims priority from, provisional application 60/022,056 filed on Jul. 22, 1996.

SUMMARY OF THE INVENTION

This invention is concerned with a novel process for the synthesis of compounds 9 and 10, both key intermediates in the synthesis of an important β3-agonist, 11, useful in the treatment of diabetes and obesity:

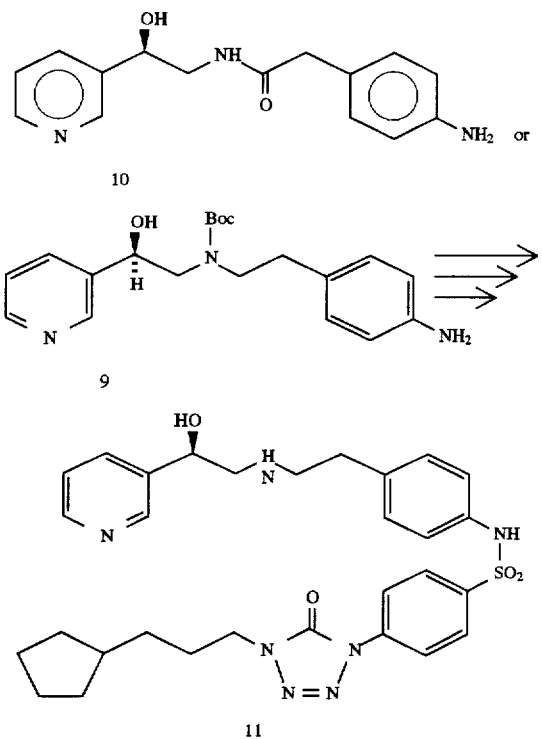

The novel process comprises a 9-step and a 7-step synthesis suitable for the large scale preparation of 9 and 10 in an overall yield of about 35% and 30% respectively from 3-acetylpyridine.

Among the highlights of this synthesis are: (1) a five-step chromatography-free α-amido ketone synthesis, which affords the bioreduction substrate ketone 5 in 65% overall yield via a Neber rearrangement reaction;

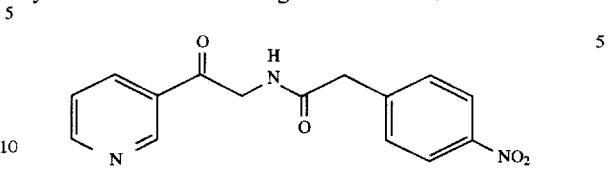

(2) a chemoselective hydrolysis of the ketal 4 to give 5 without hydrolysis of the amide;

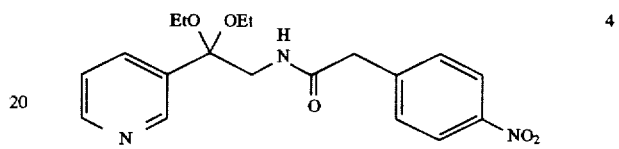

and (3) an enantioselective yeast-mediated reduction, which affords the chiral alcohol 6 from the ketone 5 in ≧94% conversion at >98% ee.

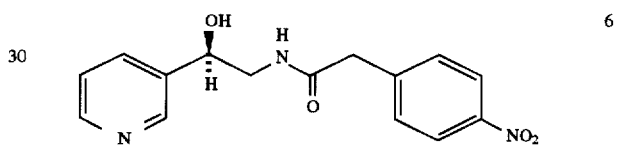

BACKGROUND OF THE INVENTION

The β3-agonist, 11, and the key intermediates, 9 and 10, produced by the novel process of this invention, are known compounds, being described in Patent Publication WO 95/29159. Processes for the preparation of Compounds 9, 10 and 11 are also disclosed in WO 95/29159. However, the process to the intermediate 9 involves a chiral borane reduction of a pyridyl chloromethyl ketone hydrochloride, followed by formation of the epoxide from the resulting chloromethyl pyridyl methanol and then opening of the epoxide with the appropriate amine.

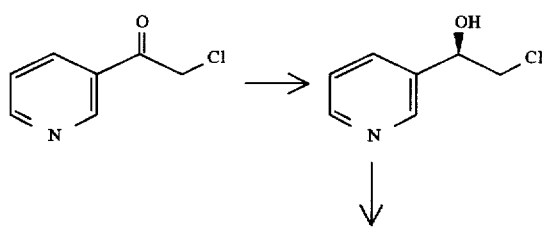

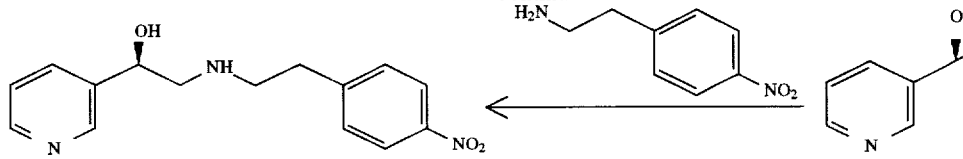

This synthesis suffered low overall yield due to competing reactions and the requirement of multiple silica chromatographies to obtain usable product. Specifically, the pyridyl chloromethyl ketone tends to polymerize during the reduction reaction, the resulting product mixture required tedious purification before it could be used; the epoxide opening reaction gave a plethora of products due to poor chemoselectivity; and the higher reactivity of the resulting secondary amines toward further alkylation. In the chiral borane reduction of the ketone, the best enantioselectivity obtained was only 89% enantiomeric excess (ee). This synthetic route clearly is not suitable for large scale preparation.

Now, with the present invention, there is provided a nine step synthesis suitable for the large scale synthesis of 9, from readily available starting materials and reagents requiring only one silica filtration. In addition, Compound 10, also a key intermediate to 11, can be synthesized in seven steps in a similar fashion.

DETAILED DESCRIPTION OF THE INVENTION

The novel process of this invention is depicted by the following reaction scheme:

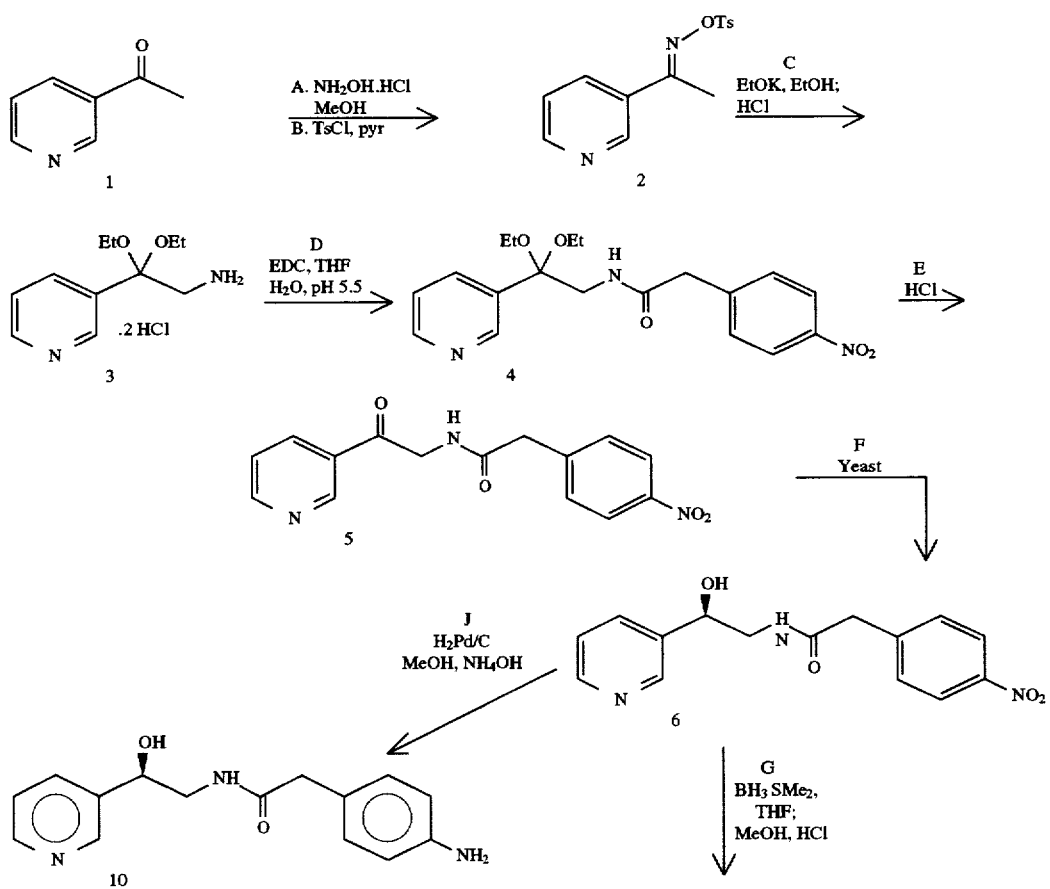

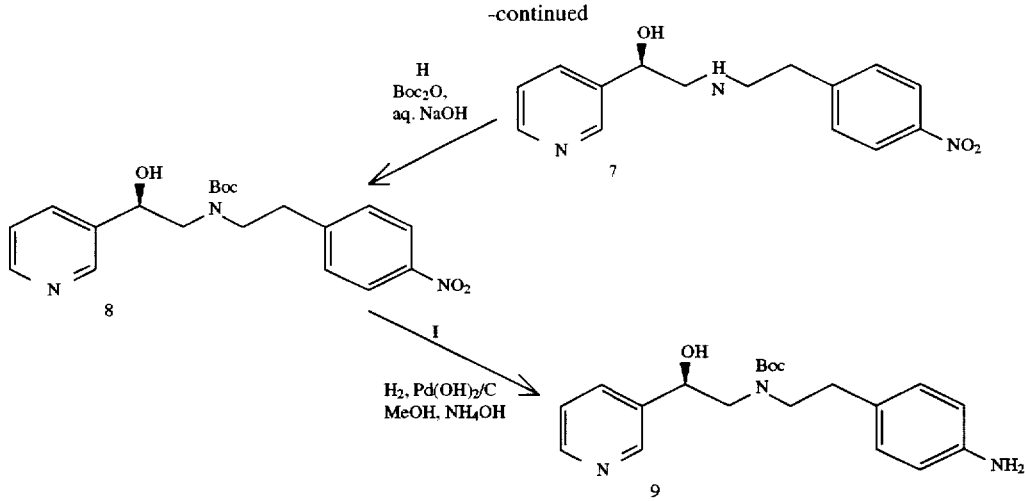

Step A of the novel process comprises formation of the tosylate of pyridine-3-acetoxime by treatment of 3-acetylpyridine with hydroxylamine hydrochloride in a $C_{1-3}$ alkanol, preferably methanol or pyridine at about 50°–80° C. to form the oxime, followed in Step B by treatment of the oxime with a sulfonylating reagent such as methanesulfonyl chloride, benzene sulfonyl chloride, or toluene sulfonyl chloride, preferably the latter in the presence of an organic base such as pyridine, triethylamine, diisopropyl ethyl amine, preferably pyridine or an inorganic base such as sodium or potassium hydroxide, sodium carbonate or the like, for about 16 to 36 hours.

Step C comprises a Neber rearrangement of the oxime sulfonate 2, to the aminoketal 3, by treating 2 with a potassium or sodium alkoxide such as potassium or sodium ethoxide, potassium or sodium methoxide, or potassium or sodium hydroxides in the corresponding alkanol at about 0°–10° C. followed by warming to 20°–30° C. with stirring for about 1–3 hours. An ether such as diethyl ether, THF or methyl t-butyl ether (MTBE) is added and the insoluble potassium tosylate is separated and the mother liquors are treated with gaseous HCl and the mixture is aged for about 6–18 hours.

In Steps D and E the aminoketal salt in water is treated with base to about pH 10 and then with 4-nitrophenylacetic acid followed by 1-hydroxybenzotriazole (HOBT) and 1-(3-dimethylaminopropyl)-3-ethylcarbodiimide (EDC) or DCC. After stirring about 10–24 hours at about room temperature, isopropyl acetate is added. The organic layer is separated and washed with saturated sodium bicarbonate and then extracted with 2N aqueous hydrochloric acid. The aqueous layer is concentrated under vacuum at about 40° C. which hydrolyses the ketal to give 5. Neutralization to pH 8 with dilute NaOH causes precipitation of the product 5.

Step F comprises an assymmetric reduction of the pyridine acyl group to the corresponding (R)-alcohol 6, with about 96% enantiomeric excess by treatment of 5 with yeast MY1833 from the culture collection of Merck & Co., Inc. It is a *Candida sorbophila* assigned ATCC accession number 74362 from a deposit made Apr. 4, 1996. The process comprises treating 5 with the yeast in a nutrient medium at about 6.0–6.5 at about 25°–35° C. for about 40–48 hours when the substrate has essentially disappeared.

This step of the overall process claimed herein forms the subject matter of a separate patent application filed concurrently herewith and identified as Attorney Docket No. 19607PV.

Step G comprises the reduction of the amide carbonyl group of 6 with a reducing agent such as boranedimethyl sulfide complex in an ethereal solvent such as THF, or diethyl ether to yield 7.

Step H is a simple Schotten-Bauman reaction between the amine 7 and $(Boc)_2O$ to yield the N-protected compound 8.

Step I comprises reduction of the nitro group of compound 8 with hydrogen in the presence of the noble metal catalyst such as palladium hydroxide on carbon, palladium on carbon, or Raney nickel, to yield 9.

Step J comprises reduction of the nitro group of compound 6 with hydrogen in the presence of the noble metal catalyst such as palladium hydroxide on carbon, palladium on carbon, or Raney nickel, to yield 10.

EXAMPLE 1

Step A: Oxime Formation

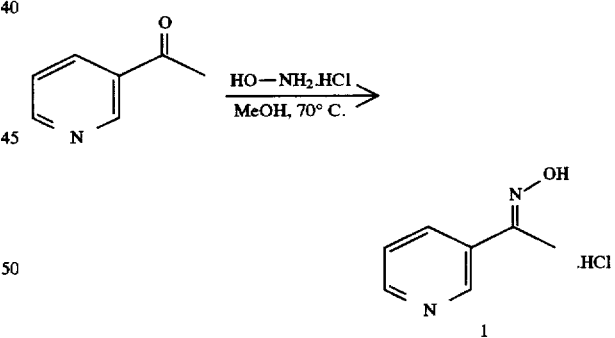

Method I

To a 1 L three-necked round bottom flask equipped with an overhead stirrer, nitrogen inlet, and a Teflon thermocouple was charged 3-acetylpyridine (110 g, 0.908 mol), methanol (550 mL) and hydroxylamine hydrochloride (65 g, 0.935 mol) at +20° C. The mixture exothermed to +35° C. The resulting mixture was heated to reflux (~70° C.) for 5 h. The reaction was monitored by HPLC and the reaction was deemed complete when 3-acetylpyridine was <0.2 area% (oxime 1 was >98 area%). The reaction was actually completed within 1 h by HPLC analysis.

Column: 4.6 mm×25 cm YMC ODS-AQ

Eluent A: MeCN

Eluent B: pH 6.0 phosphate buffer, 15 mM
Gradient: 5% A to 80% A over 20 min with 3 min hold
Injection: 20 mL
Flow rate: 1.0 mL/min
Detection: 220 nm
Temperature: 23° C.
Retention Times:
   3-acetylpyridine 10.0 min
   Oxime (E) 1 10.8 min After the reaction was complete, the batch was cooled to +22° C. (white precipitate crashed out). The batch was solvent-switched to pyridine by first concentrating to about one third of original volume under reduced pressure at 50°–60° C. and then flushed with 2×250 mL dry pyridine (KF<50 mg/L) until no methanol present (analysis by 1H NMR (CDCl$_3$)). The final volume was adjusted to 440 mL with a final KF<2 mg/mL (<5 mol % water). The mole ratio of pyridine to oxime 1 was ~5. This homogeneous solution was used as is in the next step.

Method II

Same as Method I except Methanol was replaced with pyridine upon reaction completion, the mixture was flushed with dry pyridine until <5 mol % H$_2$O.

Step B: Tosylate Formation

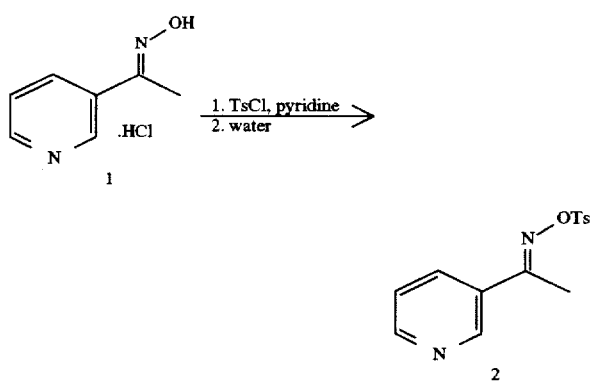

The oxime 1 solution from the previous step in a 1 L three-necked round bottom flask equipped with an overhead stirrer, nitrogen inlet, and a Teflon thermocouple was cooled in a water bath (+25° C.) while tosyl chloride (1991.1 g, 1.044 mol) was slowly added over 10 min. The reaction exothermed to +37° C. over the first 15 min then returned to room temperature.

Column: 4.6 mm×25 cm YMC ODS-AQ
Eluent A: MeCN
Eluent B: pH6.0 phosphate buffer, 15 mM
Gradient: 5% A to 80% A over 20 min with 3 min hold
Injection: 20 mL
Flow rate: 1.0 mL/min
Detection: 220 nm
Temperature: 23° C.
Retention Times:
   3-acetylpyridine 10.0 min
   Oxime (E) 1 10.8 min
   Tosyloxime (E) 2 19.8 min The reaction mixture was aged at +25° C. for 16 h at which time oxime 1 was <0.5 LC area%. Water (2.2 L) was then slowly added over 2 h. The mixture exothermed to +34° C. during the addition of the first 250 mL water then returned to +25° C. The resulting slurry was aged for an additional 2 h and then filtered (M porositys intered glass funnel) and washed with water (2×440 mL). ML losses were negligible. Product 2 was dried under vacuum at +25° C. with a N$_2$ sweep over two days. Isolated yield was 246 g (93%) with >95 LC area% purity and a KF of 0.5 mg/g (0.7 mol % water).

Step C: Neber Rearrangement

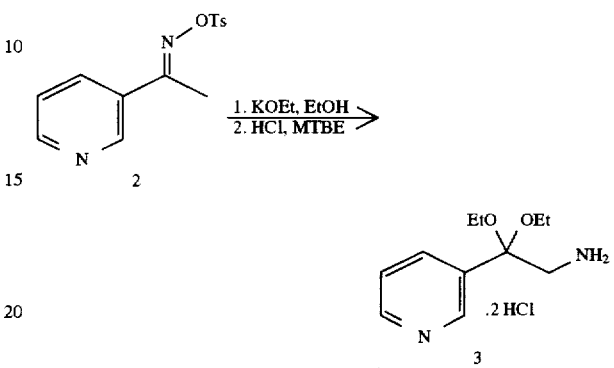

To a 5 L three-necked round bottom flask equipped with an overhead stirrer, nitrogen inlet, and a Teflon thermocouple was charged ethanol (1.0 L, KF 0.16 mg/mL) and then it was cooled to +20° C. Potassium ethoxide (84.2 g, 1.0 mol) was added through a funnel over 1 min and the internal temp. rose to +44° C. The funnel was rinsed with 0.7 L ethanol. The resulting clear solution was cooled to 5° C. and the solid tosylate 2 (238 g, KF 330 mg/g) was added over 40 min while maintaining an internal temperature of <10° C., followed by an ethanol rinse (0.2 L). During this period, potassium tosylate formed and the reaction mixture became very viscous. After stirring at +20° C. for 2.5 h, MTBE (1.64 L, KF 40 mg/mL) was added and the mixture aged for an additional 1 h. The reaction mixture was filtered through dry Solka-Floc (30 g, pre-washed with 330 mL dry MTBE) under a nitrogen blanket. The filtration took 50 min and the cake was then washed with MTBE (0.5 L).

The filtrate was transferred into a 12 L three-necked round bottom flask equipped with an overhead stirrer, nitrogen inlet, and a Teflon thermocouple and cooled to +10° C. 1M HCl in ether solution (2.3 L, 2.3 mol) was added over 45 min while maintaining an internal temperature of <+20° C. The resulting red-orange slurry was then stirred at +20° C. overnight (15 h). The product was filtered and washed with MTBE (2×500 mL) and vacuum dried under a N$_2$ sweep. The isolated yield of 3 was 230 g (99%) as an orange solid.

Purity of ketal 3 was difficult to assess based on HPLC. Analysis by 1H and $^{13}$C NMR indicated product 3 is >95% pure.

HPLC Retention Times: amino ketal 3 10.3 min (& 3.5 min Ketone?) potassium tosylate 8.7 min Step D: Amide Formation

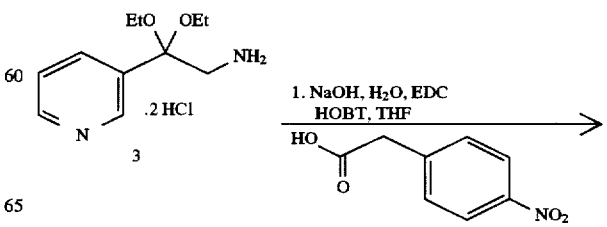

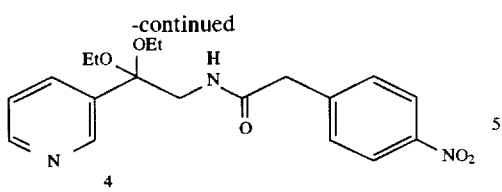

To a 5 L three-necked round bottom flask equipped with an overhead stirrer, nitrogen inlet, and a Teflon thermocouple was charged amino ketal 3 (208.3 g, 0.736 mol) and water (1.18 L). The orange-brown mixture was cooled to 5°–10° C. and 5N NaOH (264 mL) was added slowly while maintaining internal temperature<+28° C. until the pH of the mixture reached 10–12. While maintaining the reaction mixture around 15°–20° C., p-Nitrophenyl acetic acid (146.56 g, 0.809 mol) was then added, which did not completely dissolve (pH 6.6), followed by HOBT hydrate (9.95 g, 73.6 mmol, pH 5.8).

THF (500 mL) was then added (pH 5.4) followed by EDC (211.65 g, 1.104 mol) and a THF rinse (240 mL) (pH 5.0). The ice bath was removed after 30 min and reaction mixture was aged at +22° C. overnight (18 h).

Column: 4.6 mm×25 cm YMC ODS-AQ
Eluent A: MeCN
Eluent B: pH6.0 phosphate buffer, 15 mM
Gradient: 5% A to 80% A over 20 min with 3 min hold
Injection: 20 mL
Flow rate: 1.0 mL/min
Detection: 220 nm
Temperature: 23° C.
Retention Times:
  amino ketal 3 10.3 min (& 3.5 min Ketone?)
  HOBT 4.5 min
  p-nitrophenylacetic acid 8.9 min
  amido ketal 4 18.2 min
  keto-amide 5 13.7 min Saturated NaHCO₃ (1.6 L) solution was added (pH 7.4) and the pH adjusted to 8.7 with 400 mL saturated NaHCO₃ solution and 20 mL 5N NaOH. IPAC (1.6 L) was added and the mixture stirred for 15 min. The aqueous layer was cut and back extracted with IPAC (1.6 L). The combined organic layer was washed with saturated NaHCO₃ solution (0.8 L) and followed by half-saturated NaCl solution (0.8 L). The aqueous layer was cut and the organic solution was used as is in the next step. Solution assay indicated a 80:1 mixture of ketal 4 and the keto amide 5, and the combined yield is around 93%.

Step E: Ketal Hydrolysis

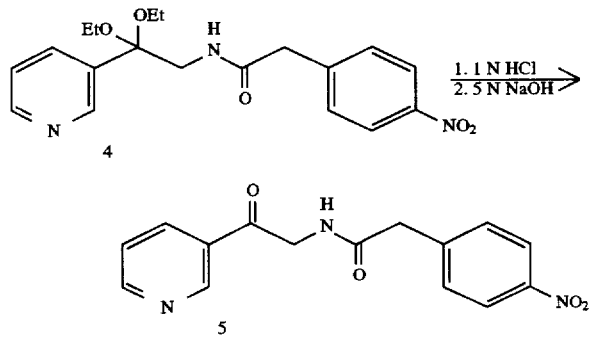

Amido-ketal 4 (IPAC solution) was extracted three times with 1N HCl (1×1.5 L and 2×0.75 L). The combined aqueous was concentrated under vacuum at 40°–45° C. The residue was flushed with 600 mL water, after which no ketal 4 was detected by HPLC.

Column: 4.6 mm×25 cm YMC ODS-AQ
Eluent A: MeCN
Eluent B: pH 6.0 phosphate buffer, 15 mM
Gradient: 5% A to 80% A over 20 min with 3 min hold
Injection: 20 mL
Flow rate: 1.0 mL/min
Detection: 220 nm
Temperature: 23° C.
Retention Times:
  p-nitrophenylacetic acid
  amido ketal 4 18.2 min
  keto-amide 5 13.7 min The volume of the batch was adjusted to 2.2 L and cooled to 10° C. (pH 0.04). With stirring, the pH was adjusted to 8.0 with 5N NaOH (430 mL, 2.15 mol), during which time the product crystallized from solution. The mixture was aged overnight and the light brown crystalline keto-amide 5 was filtered and the wet cake was washed with water (2×500 mL). The material was dried under vacuum with N₂ sweep at +22° C. over 3 days to afford 182.9 g (~90 wt %) for an isolated yield of 75% for the two steps (on <70 g scales, typical yields were 80–83%.

Step F: Yeast-mediated Reduction

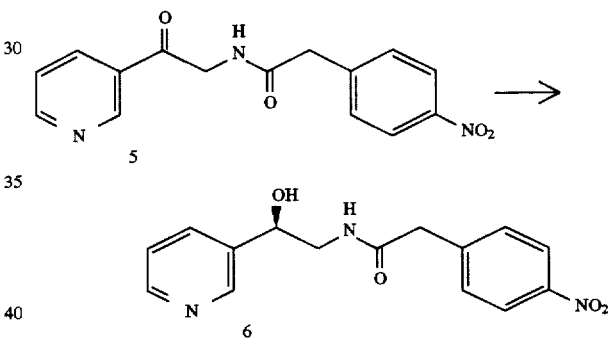

Growth of Seed Train

The contents of one 1-mL frozen vial of Y1833 (*Candida sorbophila*) in Saboraud Dextrose Broth were added to a 250-ml Erlenmeyer flask containing 50 ml of STAT1 medium described below that had been autoclaved for 30 minutes at 121° C. The culture was allowed to grow for 24 hours at 30° C. on an orbital shaker at 200 RPM. From this flask, 10 mL of inoculum were added to a 2-L Erlenmeyer flask containing 500 ml of STAT1 medium that had been autoclaved for 30 minutes at 121° C. This culture was also allowed to grow for 24 hours at 30° C. on an orbital shaker at 200 RPM. The contents of this flask were used as inoculum for a 16 L fermentation.

STAT1 medium consists of monosodium glutamate (20 g/L); MOPS (20 g/L); yeast extract (7 g/L); glucose (2 g/L); P-2000 (2 ml/L); Magnesium chloride hexahydrate (1 g/L); calcium chloride dihydrate (0.5 g/L); cupric chloride dihydrate (0.5 g/L); and potassium chloride (0.5 g/L).

Fermentations

The fermentation broth (16 L) was added to the fermentation tank and sterilized for 35 min. at 123° C. The pH of the broth was adjusted to 6.0–6.5 by the addition of HCl. In addition to a 6.5 pH, the other initial conditions of the fermenters were an agitation of 600 RPM, an airflow of 4 L/min, a temperature of 30° C., and a pressure of 1 bar. The dissolved oxygen in the fermenter was maintained above 30% of saturation through automated agitation control in the range between 600 and 700 RPM.

A substrate addition assembly was constructed by connecting a fermenter needle to approximately four feet of silicone rubber tubing (0.192" I.D.×0.392" O.D.) attached to a 2-L bottle with a bottom spout, and to this 320 mL of pH 2 deionized water and a magnetic stir bar were added. The deionized water was acidified with phosphoric acid prior to adding it to the bottle. The assembly was autoclaved for 30 minutes at 121.5° C. After the equipment had cooled to room temperature, 40 g ketone substrate were measured in a weigh boat and added to the bottle using a metal spatula under a sterile hood. The weigh boat and spatula were then rinsed with 320 mL ethanol which was also added to the bottle under a fume hood. The assembly was placed on a stir plate that was used to agitate the mixture and create a suspension. The pressure in the tank was then reduced to 0.1 bar and the airflow was stopped while the suspension was pumped through the tubing and needle into the fermenter. Next, 320 mL deionized water that had been autoclaved for 30 minutes at 121° C. were poured into the bottle and stirring and pumping were resumed to wash any remaining substrate into the tank. Finally, 500 mL inoculum were poured into the bottle, and again stirring and pumping were resumed. After the culture had been transferred to the fermenter, the tubing was clamped and the pressure and airflow of the tank were returned to their initial values.

The concentrations of ketone and alcohol in broth samples were assayed by reverse phase HPLC and the e.e. of the alcohol was monitored by supercritical fluid HPLC. The runs were terminated after approximately 45 hours, when the amount of ketone in the fermenter as assayed by HPLC had reached <1% of its initial value.

Isolation

The fermentation batch was centrifuged to remove cells and fines.

Supernatant (170 mL) was extracted twice with 170 mL methyl ethyl ketone (MEK) saturated with water. The combined MEK extracts were concentrated to an aqueous slurry, sulfuric acid was added to pH2 and the slurry was extracted three times with isopropyl acetate/5% (v/v) isopropyl alcohol. The pH of the washed aqueous slurry was adjusted to 6.8 with 50% aqueous sodium hydroxide, following which fine crystalline solids gradually appeared.

The aqueous slurry was concentrated under vacuum to remove organic solvents. The room temperature aqueous slurry was filtered to collect the solid product and the filter cake was washed with cold water. Yield~70%; Purity~87%; ee 98.5%.

Step F: Alternate Yeast-mediated Reduction Process
Growth of Seed Train

The contents of one 1-mL frozen vial of Y1833 (*Candida sorbophila*) preserved in Saboraud Dextrose Broth (Difco) and glycerol (20%, v/v) at −70° C. were added to a 250-mL Erlenmeyer flask containing 50 mL of Sabouraud Dextrose Broth medium that had been autoclaved for 30 minutes at 121.5° C. The culture was allowed to grow for 24 hours at 34° C. on an orbital shaker at 200 RPM.

Fermentation

A volume of 1 liter of YNB medium [monosodium glutamate (93 g/L); citrate monohydrate (20 g/L); yeast nitrogen base w/o amino acids and ammonium sulfate (15 g/L); P-2000 (10 mL/L); cupric chloride dihydrate (15 mg/L)] was added to the bioreactor (2 liter) and sterilized for 30 min. at 123° C. Glucose that had been sterilized separately was added upon cooling to give a final concentration of 7 g/L. A volume of 20 ml of the inoculum prepared as described above was then added to the bioreactor. The microorganisms were cultivated under an agitation of 1200 RPM, an airflow of 0.5 L/min of 90% oxygen, and a temperature of 34° C., until an optical chemistry (OD) @ 600 nm in the range of 15–25 and a glucose concentration of <1 g/L were achieved. At that time, the pH of the cultivation broth was adjusted to 8.0 and maintained at that value through the addition of sterile 5N NaOH and 5N $H_2SO_4$, ethanol in the amount of 13 ml and ketone substrate in the amount of 50 g were then charged to the tank. Immediately after these additions, glucose feeding was initiated at a rate of 1 g/(l.hr) from a 280 g/l stock solution that had been autoclaved for 30 min at 121.5° C. The concentrations of ketone and alcohol in the broth were assayed by reverse phase HPLC and the e.e. of the alcohol was monitored by supercritical fluid HPLC. The runs were terminated after approximately 7 days, when the amount of ketone in the fermenter as assayed by HPLC had reached <1% of its initial value (See Step 6 for HPLC method). A final alcohol titer of 35 g/L with an ee of 98% was achieved under these conditions.

Isolation

Isolation of the product is conducted in the same manner as described in Step F.

Step G: Amide Reduction

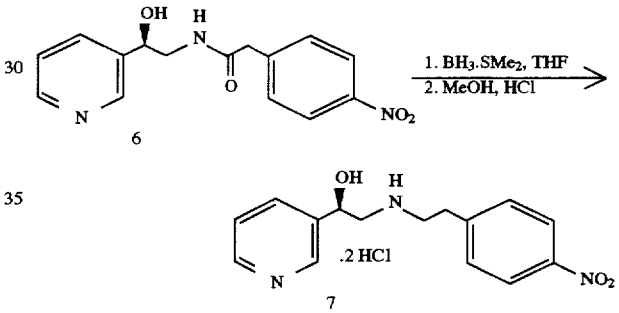

To a 72 L three-necked round bottom flask equipped with an overhead stirrer, nitrogen inlet, addition funnel, scrubber with bleach (2 gallons) and a Teflon thermocouple was charged N—(R)-(2-hydroxy-2-pyridin-3-yl-ethyl)-2-(4-nitro-phenyl)-acetamide, 6 (1480 g, 94.1%, 4.622 mol), and THF (36 L, KF 20 mg/mL). The resulting suspension was cooled to −3° to 2° C., and borane-dimethylsulfide, 9.97M (2.3 L) was added via an addition funnel over 50–60 min while maintaining the reaction temperature at −1° to +3° C. The batch was then allowed to warm to 24° C. and aged at ambient temperature for 12 h.

The reaction mixture turned into a clear solution after the temperature reached 18°–20° C. In order to monitor reaction completion, a 0.5 mL batch sample was taken and quenched with 0.5 mL MeOH followed by addition of 2 drops of 12N HCl, concentration to dryness, and flushing with MeOH (2 mL each) three to four times. The residue formed was dissolved in 2 mL MeOH. 100 μL of this solution was diluted to 10 mL with 50:50 MeCN/pH6 aq. buffer and assayed by HPLC.

Column: 4.6 mm×25 cm YMC ODS-AQ

Eluent A: MeCN

Eluent B: pH6.0 phosphate buffer, 15 mM

Gradient: 10% A to 94% A over 24 min and kept this ratio for another 9 min

Injection: 20 mL

Flow rate: 1.0 mL/min

Detection: 220 nm

Temperature: 23° C.

Retention Times:

Alcohol amine 7 13.0 min

Alcohol amide 6 13.7 min

After reaction was complete, the batch was cooled to −2° to +3° C. and quenched by adding MeOH (7.5 L) over 20 min, while maintaining the internal temperature 5° C. The mixture was then warmed up to room temperature and filtered through a sintered glass funnel (10–30 mM) to remove solid impurities. The filtrate was transferred back to the flask afterwards and concentrated to about one third of the original volume, and then flushed with methanol (2×25 L) to remove methyl borate.

Caution: The first few liters of methanol addition generated large amounts hydrogen gas bubbling; thus MeOH must be added very slowly at the beginning. If the batch contains insoluble dark particles a filtration should be implemented to remove these solid impurities.

12N HCl (1.18 L) was added with caution over 10 min. and the batch temperature below 10° C. was kept; gas evolution also occurred. The batch solution color turned much lighter afterwards. The reaction mixture was aged at room temperature for 1 h.

The resulting solution was concentrated under vacuum pressure (25–27 in.) and the internal temperature was kept below 40° C. The batch volume was reduced to approximately one third (16 L) of its original and flushed with MeOH 2×25 L.

The batch solution must be followed by HPLC to make sure all borane-product complexes are broken (only one product major peak on the LC chromatogram), otherwise more MeOH flushes might be necessary.

The batch in MeOH was diluted with about 20 L of DI water to 35 L and MeOH was removed by vacuum distillation. The batch volume was reduced to ⅓ of its original volume and the temperature was kept below 55° C. The batch was diluted with DI water to 18–19 L and adjusted to pH4.5–5.0 with 50% NaOH (410 mL). The resulting aqueous solution was extracted once with 15 L MTBE and the total volume of the aqueous solution was around 20 L and was ready for the next step reaction. 1522 g pyridine alcohol p-nitrophenyl amine di-HCl salt 7 in aq. solution was obtained (91.5%).

The MeOH level in the aqueous solution was determined by $^1$H NMR (D$_2$O). The molar ratio of MeOH to the product was 1:4.4 or 2 mL/L in this batch.

| Product purity: | Compound | LC retention time | Area % |
|---|---|---|---|
| | Amine 7 | 13.2 min | 94 |
| | Amide 6 | 13.8 min | 1.0 |

Step H: Boc protection

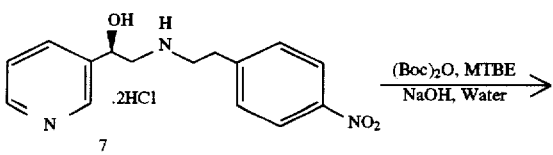

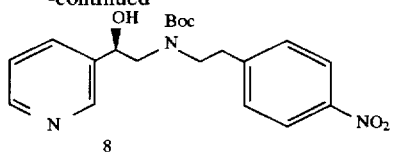

To a 50 L round bottom flask equipped with an overhead stirrer, an N$_2$ inlet, and a Teflon thermocouple was charged an aqueous solution of 7 (1520 g, 4.22 mol) and t-butyl methyl ether (12 L). The two phase mixture was kept below 20° C. with an ice-water bath and 5N NaOH was added over 15–20 min. When the pH neared 11–12, the addition rate should be very slow since it took longer to reach equilibrium. After the final pH was 12.5–13.0, the batch was cooled to 3°–5° C. and di-t-butyl dicarbonate (967 g) was charged in one portion. The batch pH gradually lowered to 8.0–8.5 after the Boc anhydride addition. The reaction was monitored by HPLC (sample preparation: 20 μL top layer in 10 mL 50/50 acetonitrile/pH6 buffer). The ratio of 8 to 7 at end of the reaction was >98.5:1.5 (area%). The reaction normally takes 3–4 h.

Column: 4.6 mm×25 cm YMC ODS-AQ

Eluent A: MeCN

Eluent B: pH6.0 phosphate buffer, 15 mM

Gradient: 10% A to 94% A over 24 min and kept this ratio for another 9 min.

Injection: 20 mL

Flow rate: 1.0 mL/min

Detection: 220 nm

Temperature: 23° C.

Retention Times:

Alcohol amine 7 13.0 min

Alcohol Boc-amine 8 21.3 min

After the reaction was completed, the mixture was transferred to a 50 L separatory flask, and the layers were cut. The aqueous layer was extracted with MTBE once (12 L). The combined organic layer was washed with 0.2M NaH$_2$PO$_4$ (1×12 L) followed by saturated sodium bicarbonate (1×12 L). The batch was then transferred back to the main 50 L flask and concentrated to about one third of the original volume. It was turned over to a methanol solution by adding 20 L MeOH and flushing with methanol 2×10 L. The final volume was adjusted to 30 L with addition of MeOH and 1599 g (95.3%) of product in the yellow solution was obtained and ready for the next step reaction. The total product loss in the three aqueous layer was less than 0.5%.

MTBE layer before aqueous phosphate wash:

| Compound | LC retention time | Area % |
|---|---|---|
| Amine 7 | 13.2 min | 2.4 |
| Amineboc 8 | 21.4 min | 86 |
| Bis-boc 9a | 23.3 min | 2.6 |
| Amide 6 | 13.8 min | 0.6 |

The batch after wash and turnover to MeOH:

| Compound | LC retention time | Area % |
|---|---|---|
| Amine 7 | 13.2 min | 0 |
| Amide 6 | 13.7 min | 0.3 |
| Amineboc 8 | 21.3 min | 96.7 |
| Bis-boc 9a | 23.1 min | 2.5 |

Step I: Hydrogenation of 8

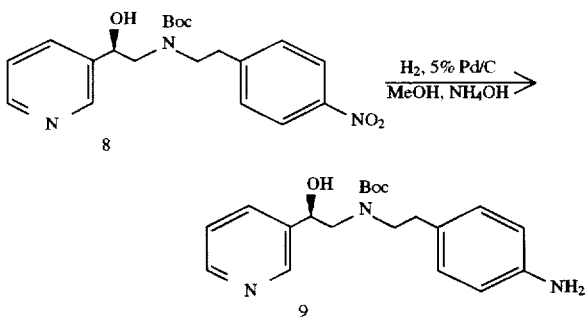

To a 5 gallon autoclave vessel was charged the substrate methanol solution of 8 (9.5 L, 1.22 mol), 28% ammonium hydroxide (255 mL, 1.83 mol) and 5% palladium on carbon (19 g). The hydrogen pressure was set to 20 psi, and the first two equivalents of hydrogen gas uptake were done at 25° C. After that the reaction temperature was raised to 40°–45° C. until a total of all three equivalents hydrogen uptake was reached. The reaction was monitored by both HPLC and NMR. The hydrogenation normally took 20–24 h to complete. HPLC sample preparation: 100 µL filtered clear reaction solution (Whatman syringe filter 0.45 mM PTFE) was dissolved in 50/50 acetonitrile/pH6.0 buffer to 10 mL. The ratio of the product to starting material HPLC area percentage should be greater than 99.5:0.5.

Column: 4.6 mm×25 cm YMC ODS-AQ

Eluent A: MeCN

Eluent B: pH6.0 phosphate buffer, 15 mM

Gradient: 10% A to 94% A over 24 min and kept this ratio for another 9 min.

Injection: 20 mL

Flow rate: 1.0 mL/min

Detection: 220 nm

Temperature: 23° C.

Retention Times:
  Boc amine aniline 9 17.6 min
  Alcohol Boc-amine 8 21.3 min

After the reaction was complete the batch was transferred out and filtered through a 3 L medium fritted disc Buchner funnel with 280 g Solka Floc (prewashed with 1 L MeOH) to remove the solid catalyst. The wet cake was rinsed with 2 L MeOH. The combined filtrate and wash was stored under nitrogen atmosphere at room temperature.

In a 50 L round bottom flask equipped with an overhead stirrer, a Teflon thermocouple, a steam heater, and an ethylene glycol cooling unit all filtrates and washes from three batches were combined and concentrated to 5–7 L. The batch was then flushed 4 times with EtOAc (10 L each) until MeOH was not detected by $^1$H NMR (3.3–3.4 ppm chemical shift, 3H in CD$_3$OD). The final batch volume was adjusted to 5–7 L with EtOAc.

To a 29×100 cm (inner diameter×height) glass column with a pressure gauge, eluting solvent inlet and pressurized nitrogen gas inlet was loaded a slurry of silica gel (18 kg as a dry powder) in 50/50 EtOAc/Hexanes (a total 60 L mixed solvent was used) by a pneumatic pump. Another 1 to 1.5 bed volume of the same solvent was added afterwards and the silica gel bed was allowed to settle overnight. The top silica gel bed was then covered with 2 cm thick sand (3.6 Kg) to prevent possible disturbance later on while charging crude product and solvent. 7.3 L Batch/EtOAc solution was diluted to 9 L with hexanes and loaded to the top of the column followed by washing with 1 L 50/50 EtOAc/Hexane. As soon as the compound was loaded the fraction collecting was started. The column pressure was adjusted to 2.5–3 psi and the flow rate was about 1.2 L/min.

| 50/50 EtOAc/Hexanes | 84 L |
| 75/25 EtOAc/Hexanes | 112 L |
| 100% EtOAc | 500 L |

The volume of each fraction collected:

| Fr#1–8: | 18–19 L |
| Fr#9–15 | 10–12 L |
| Fr#16–41 | 18–19 L |

All fractions were checked via TLC plate. Among them Fr#11–41 were selected for concentration. The batch temperature was controlled at 5°–30° C. while the vacuum was 29.5–25 in. during the process. When the volume reached 5–7 L, the batch was flushed with 4×11 L MTBE until the EtOAc level was 10 mol % of the product (calculated by $^1$H NMR). The product in MTBE solution was adjusted to 15 L (11.84 kg) and gave 10.92 wt % (net 1.29 kg, 3.62 mol) with 96% yield on the hydrogenation plus column purification. The solution was ready for the next coupling reaction step.

Step J: Hydrogenation of 6

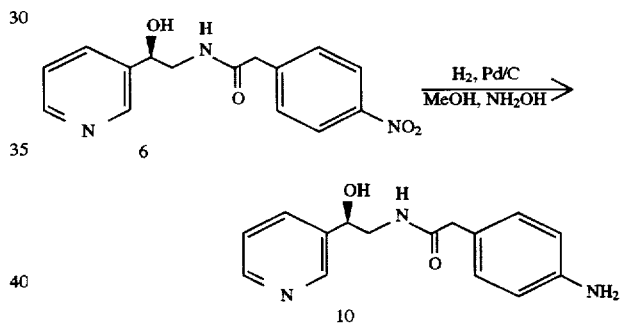

To a 250 mL hydrogenation bottle was charged N—(R)-(2-hydroxy-2-pyridin-3-yl-ethyl)-(2-(4-nitro-phenyl)-acetamide (6) (5 g, 16.6 mmol), methanol, (90 mL), 28% ammonium hydroxide (3.5 mL, 24.9 mmol) and 5% palladium on carbon (0.2 g). The hydrogen pressure was set to 20 psi and the reaction was heated at 35°–45° C. until a total of three equivalents hydrogen uptake was reached. The reaction was monitored by HPLC. The hydrogenation normally took 6–10 h to complete.

Column: 4.6 mm×25 cm YMC ODS-Aq

Eluent A: MeCN

Eluent B: pH6.0 phosphate buffer, 15 mM

Gradient: 10% A to 94% A over 24 min. and kept this ratio for another 9 min.

Injection: 20 mL

Flow rate: 1.0 mL/min.

Detection: 220 nm

Temperature: 23° C.

Retention Times:
  Amide aniline 10 9.6 min.
  Nitrophenyl amide 6 13.9 min.

After the reaction was complete the batch was filtered through a layer of Solka Floc (1 g, prewashed with 10 mL MeOH) to remove the solid catalyst. The wet cake was rinsed with 25 mL MeOH. The combined filtrate and wash (122 mL) was concentrated to 40 mL under vacuum at 30°–45° C. (internal temperature). The crystalline solid product gradually formed during the distillation. The batch was then flushed two times with EtOAc (34 mL each) and two times with 10/90 MeOH/EtOAc until the batch supernatant was 1–1.5% water (KF=1000–1500 µg/100 µL). The batch volume was adjusted to 30–34 mL with 10/90 MeOH/EtOAc. After the batch was stirred at room temperature for 14 h. it was filtered (10–15 µM). The wet cake was washed with 15 mL MeOH and dried under vacuum with a nitrogen bleed. Product B. N—(R)-(2-hydroxy-2-pyridin-3-yl-ethyl)-(2-(4-amino-phenyl)-acetamide. (4.29 g) was recovered as a yellow-tan crystalline solid with 99+% purity and 93–95% yield. The M.L. and wash loss was 1.5–2%.

What is claimed is:

1. A process for the preparation of a compound of structural formula:

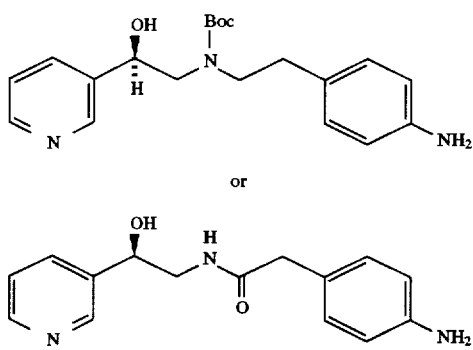

or

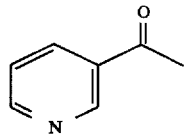

which comprises the steps of:

Steps A and B: treating the compound of formula 1:

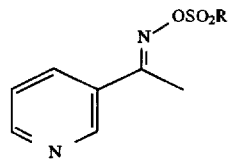

with hydroxylamine hydrochloride in a $C_{1-3}$ alkanol. followed by treatment with $RSO_2Cl$ in the presence of a base. wherein R is methyl. benzene or toluene to form the compound of formula 2:

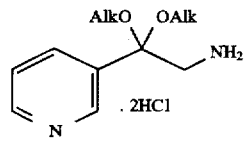

Step C: treating 2 with a potassium $C_{1-3}$ alkoxide in the corresponding alkanol followed by treatment with HCl to form the compound of formula 3:

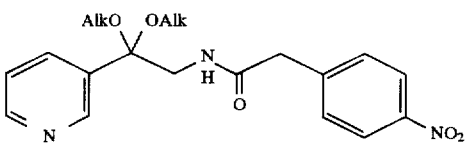

wherein Alk is $C_{1-3}$ alkyl;

Step D: treating 3 with 4-nitrophenylacetic acid. HOBT and EDC or DCC to form the compound of formula 4;

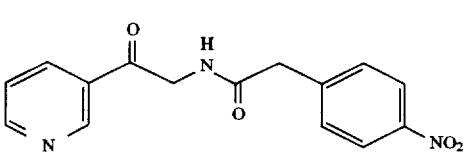

Step E: treating 4 with HCl to produce the compound of formula 5:

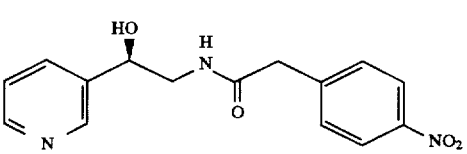

Step F: treating 5 with *Candida Sorbophila* yeast. ATCC Accession No. 74362 to produce the compound of formula 6:

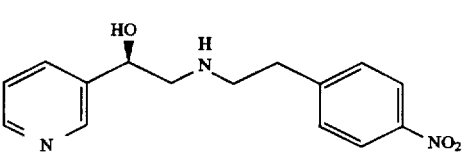

Step G: treating 6 with borane dimethylsulfide complex to produce the compound of formula 7:

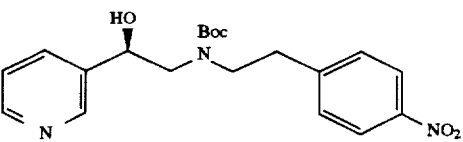

Step H: treating 7 with $(BOC)_2O$ to produce the compound of formula 8:

and

Step I: treating 8 with hydrogen in the presence of a noble metal catalyst to produce the compound of formula 9; or Step J: treating 6 with hydrogen in the presence of a noble metal catalyst to produce the compound of formula 10.

2. The process of claim 1 wherein, in Step A. R is toluene; in Step C. Alk is ethyl and the potassium $C_{1-3}$ alkoxide is potassium ethoxide.

* * * * *